US00PP11301P

United States Patent [19]

Boeder

[11] Patent Number: Plant 11,301

[45] Date of Patent: Mar. 21, 2000

[54] CHRYSANTHEMUM PLANT NAMED 'LOVEBIRD'

[75] Inventor: Mark Boeder, West Wittering, United Kingdom

[73] Assignee: Cleangro Limited, West Sussex, United Kingdom

[21] Appl. No.: 09/038,789

[22] Filed: Mar. 11, 1998

[51] Int. Cl.[7] ..... A01H 5/00

[52] U.S. Cl. ..... Plt./290

[58] Field of Search ..... Plt./287, 286, 290, Plt./296

*Primary Examiner*—Howard J. Locker
*Attorney, Agent, or Firm*—Christie, Parker & Hale, LLP

[57] ABSTRACT

A new plant variety of Chrysanthemum producing dark coral flowers.

1 Drawing Sheet

BACKGROUND OF THE INVENTION

The present invention is directed to a new and distinct variety of Chrysanthemum botanically classified as *Dendranthema grandiflora*. The varietal denomination of the new chrysanthemum is 'Lovebird'.

The female parent of the new variety is an unnamed, undistributed seedling identified as 'G12-C1' and the male parent is an undistributed, unnamed, seedling identified as 'G23-C1'. The new variety has been asexually reproduced by vegetative cuttings in Ventura County, Calif. and the distinguishing characteristics are retained through successive generations of asexual reproduction.

SUMMARY OF THE INVENTION

'Lovebird' is a pot type Chrysanthemum plant variety that produces dark coral flowers.

BRIEF DESCRIPTION OF ILLUSTRATION

The accompanying photograph shows a typical specimen of the new variety with colors being as nearly true as possible with illustrations of this type. The flowers in the illustration do not show maximum age on the plant. Flowers are persistent and consistently open to show disc florets with maximum age.

DESCRIPTION OF THE PLANT

The following description of the new variety is of specimens grown in a greenhouse in Ventura County, Calif. in the month of October. 'Lovebird' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once ten days after planting which results in about 4 breaks per pinch. It has been observed that the shelf life of 'Lovebird' is about 24 days with the response time of about 6.5 weeks. No treatment with growth retardant is required. Useful growing conditions include night temperatures of about 64°–66° F., day temperatures of about 80°–85° F. and about 5,000 foot-candles of light.

Plant:

*Habit.*—Compact mound.
*Height.*—About 22 cm.
*Branching characteristics.*—Strong, short branching.

*Number of breaks from pinch.*—About 4.
*Typical container sizes commercially grown in.*—4", 6" pots, 1 gallon containers.
*Length of lateral branches.*—About 13 cm.
*Stem color.*—Near 138B.

Foliage:

*Leaf arrangement.*—Alternate.
*Number of leaves per lateral branch.*—About 13.
*Leaf size.*—Length: About 6.4 cm. Width: About 3.3 cm.
*Leaf shape.*—Broadly ovate, lobed.
*Attachment.*—Petioled.
*Leaf apex.*—Obtuse, with serration.
*Base.*—Tapered.
*Margin.*—Palmately lobed with infrequent serrations.
*Aspect.*—Concave.
*Surface.*—Top: Lightly pubescent. Bottom: Lightly pubescent.
*Petiole.*—Length: About 1.5 cm. Color: Near 143C.
*Other petiole characteristics.*—Tapered wings.
*Color.*—Mature leaf: Top: Near 147A. Bottom: Near 137C. Young leaf: Top: Near 137A. Bottom: Near 137D.

Flower:

*Inflorescence form.*—Cyme.
*Flower form.*—Decorative.
*Number of blooms per branch.*—About 6.
*Diameter of fully expanded bloom.*—About 4.5 cm.
*Depth of fully expanded bloom.*—About 2 cm.
*Longevity of bloom.*—About 24 days.
*Sepal number.*—About 30. Color: Near 137B. General appearance of sepals: Fleshy, very little membrane.
*Peduncle length.*—About 6.5 cm at lowest point on flowering stem, about 2.3 cm at the terminal peduncle, peduncle length is progressively longer downward toward the main stem. Habit: Straight. Surface: Pubescent. Color: Near 138B.
*Ray florets.*—Number per flower: About 180. Shape: Elliptic. Apex: Obtuse with 3 small lobes. Base: Tapered. Margin: Entire. Aspect: Slightly involute. Length: About 2 cm. Width: About 0.6 cm.
*Disc florets.*—Number per flower: About 20. Shape: Tubular. Length: About 0.5 cm. Width: About 0.1 cm.
*Fragrance.*—Strong, musky.

Flower color:

*General flower coloration.*—Dark coral; outer ray florets showing more pink, inner florets more yellow.

*Ray florets, top side.*—Immature: Near 35B with some streaking of near 32D, base near 12B. Mature: Near 35B with some streaking of near 35C. Fading: Near 34D.

*Ray floret, under side.*—Mature: Near 18C. Immature: Near 18B. Fading: Near 18C.

*Disc florets.*—Mature: Near 15B tip, near 2D base.

*Changes as the flower ages.*—Flower color becomes more yellow; flower form stays flat as ray florets open outward; eventually center disc florets are visible.

Reproductive organs:

*Ray florets.*—Pistillate. Stigma shape: Linear. Stigma color: Near 11A. Style length: About 0.4 cm.

*Disc florets.*—Stigma shape: 2 forked. Stigma color: Near 13A. Style length: About 0.2 cm. Stamen number: About 6. Anther length: About 0.15. Pollen color: Near 23A. Pollen quantity: Abundant.

What is claimed is:

1. A new and distinct Chrysanthemum plant of the variety substantially as herein shown and described.

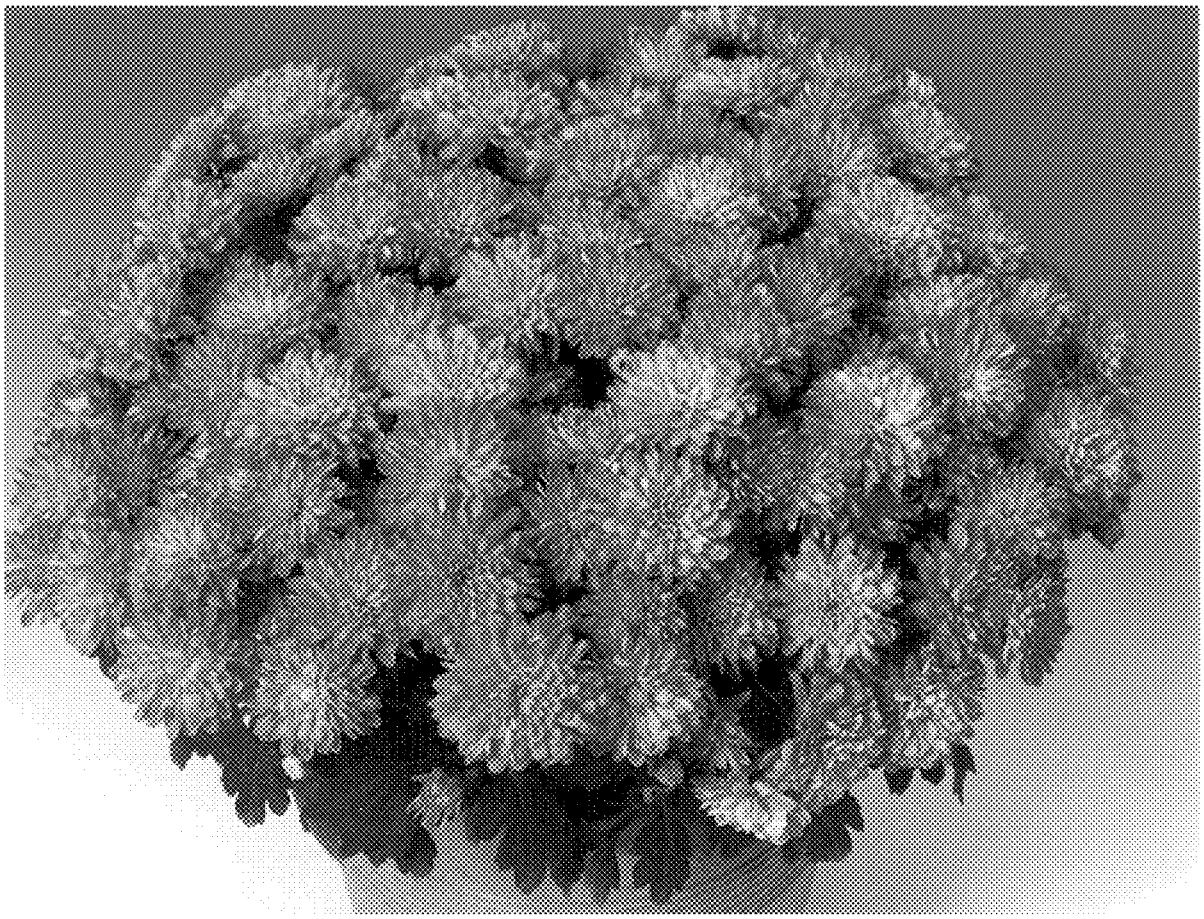

* * * * *